(12) United States Patent
Minch et al.

(10) Patent No.: US 8,039,618 B2
(45) Date of Patent: Oct. 18, 2011

(54) METHOD FOR PRODUCING BICYCLIC GUANIDINES BY USE OF A CYCLIC UREA

(75) Inventors: Britt A. Minch, Tarentum, PA (US); Charles R. Hickenboth, Cranberry Township, PA (US); Richard F. Karabin, Ruffs Dale, PA (US); Steven R. Zawacky, Pittsburgh, PA (US); Gregory J. McCollum, Gibsonia, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 387 days.

(21) Appl. No.: 12/118,082

(22) Filed: May 9, 2008

(65) Prior Publication Data

US 2009/0281313 A1    Nov. 12, 2009

(51) Int. Cl.
    *C07D 471/04*    (2006.01)
(52) U.S. Cl. ...................................................... 544/279
(58) Field of Classification Search .................... 544/279
    See application file for complete search history.

(56) References Cited

U.S. PATENT DOCUMENTS

| 4,797,487 A | 1/1989 | A'Court | |
| 2006/0276461 A1* | 12/2006 | Old et al. | 514/227.2 |

FOREIGN PATENT DOCUMENTS

EP    0198680 A    10/1986

OTHER PUBLICATIONS

Shen, et al.., JACS, 2006, 128, 13692-13693.*
Simoni, et al., Org. Ltrs., 2000, vol. 2, # 24, 3765-3768.*
Rama Rao, et al., Tet. Ltrs., vol. 34, # 31, Jul. 1993, 4993-4996.*
McKay, et al., Can. J. Chem., vol. 40 (1962), 1160-1163.*
Hövelmann, et al., Chem. Comm., 2008, 2334-2336.*
Edwards, Drug Disc. Today, vol. 11, # 11-12, Jun. 2006, 569-570.*
Kurihara, et al., Bioorg. & Med. Chem Ltrs., vol. 14, # 16, Aug. 16, 2004, pp. 4131-4134.*
Ulrich, et al., J. Org. Chem., vol. 43, #8, 1978, 1544-1546.*
Davis, et al., JACS, 1923, 45 (7), 1816-1820.*
Eusebio Juaristi et al., "Synthesis of New Chiral Derivatives of N,N'-Dimethylpropyleneurea (DMPU) and Examination . . . ", Helvetica Chimica ACTA, vol. 85, No. 7, 2002 (pp. 1999-2007).
Antonio Echavarren et al., "Anion-Receptor Molecules: Synthesis of a Chiral and Functionalized Binding Subunit, a Bicyclic Guanidinium Group Derived from L- or D-Asparagine", Helvetica Chimica ACTA, vol. 71, No. 4, 1988 (pp. 685-693).
Chong Han et al., "Synthesis of Carbamates and Ureas Using Zr(IV)-Catalyzed Exchange Processes", Organic Letters, vol. 9, No. 8, 2007 (pp. 1517-1520).
Zhengqing You et al., "New AZT Conjugates as Potent Anti-HIV Agents", Nucleosides, Nucleotides and Nucleic Acids, vol. 25, No. 1, 2006 (pp. 37-54).

* cited by examiner

*Primary Examiner* — James O Wilson
*Assistant Examiner* — Cecilia M Jaisle
(74) *Attorney, Agent, or Firm* — Diane R. Meyers; Steven W. Hays

(57) ABSTRACT

The present invention is directed to a method for producing bicyclic guanidines comprising heating a cyclic urea to a temperature >200° C. to form the bicyclic guanidines.

19 Claims, No Drawings

METHOD FOR PRODUCING BICYCLIC GUANIDINES BY USE OF A CYCLIC UREA

BACKGROUND OF THE INVENTION

1. Field of the Invention

The present invention relates to a method for producing bicyclic guanidines.

2. Background Information

It is well known that bicyclic guanidines, such as 1,5,7-triazabicyclo[4.4.0]dec-5-ene (TBD) is chemically active and, therefore, can be used to catalyze a variety of chemical reactions. An important consideration in the commercial exploitation of bicyclic guanidines as a catalyst (for any reaction) is that bicyclic guanidines be relatively inexpensive to purchase or easily produced. Published methods for synthesizing bicyclic guanidines, however, are often complicated, often involve the use of a multiple step synthesis process, and/or require the use of prohibitively expensive starting materials which may be hazardous in a variety of ways.

For example, some methods utilize carbon disulfide ($CS_2$) in the production of bicyclic guanidines. However, there are regulatory and handling issues associated with the use of carbon disulfide. For instance, air transport of carbon disulfide is typically prohibited. Additionally, contact with carbon disulfide with air should be avoided because the combination of high volatility, wide flammability range, and low ignition temperature results in a readily combustible mixture.

Accordingly, there is a need for a process for producing bicyclic guanidines at relatively high yields while not using hazardous materials, such as carbon disulfide, as an ingredient to produce the bicyclic guanidines.

SUMMARY OF THE INVENTION

The present invention is directed to a method for producing bicyclic guanidines comprising heating a cyclic urea to a temperature >200° C. to form the bicyclic guanidines.

The present invention is also directed to a method for producing bicyclic guanidines comprising providing a cyclic urea; and heating the cyclic urea to a temperature >200° C. in the presence of a non-hydrocarbon solvent to form the bicyclic guanidines.

DETAILED DESCRIPTION OF THE INVENTION

As used herein, unless otherwise expressly specified, all numbers such as those expressing values, ranges, amounts or percentages may be read as if prefaced by the word "about", even if the term does not expressly appear. Plural encompasses singular and vice versa. For example, although reference is made herein (including the claims) to "an" (aminoalkyl) amine, "a" carbonate, a combination (i.e., a plurality) of (aminoalkyl) amines and/or carbonates may be used.

As used herein, "plurality" means two or more.

As used herein, "includes" and like terms means "including without limitation."

When referring to any numerical range of values, such ranges are understood to include each and every number and/or fraction between the stated range minimum and maximum.

The present invention is directed towards a method of producing bicyclic guanidines. Specifically, the present invention is directed towards a method of producing bicyclic guanidines that comprises heating a cyclic urea to a temperature >200° C. It has been surprisingly found that the production of bicyclic guanidines through the process disclosed herein can provide a yield of ≧85%, such as from 90% to 95%, of the bicyclic guanidine reaction product. Another advantage of the disclosed process is that the process does not require the use of carbon disulfide or other hazardous materials in order to produce bicyclic guanidine. Accordingly, any regulatory and/or environmental issues associated with the use of carbon disulfide are avoided.

As stated above, the process disclosed in this invention comprises heating a cyclic urea to a temperature >200° C., such as from 218° C. to 240° C., in order to form the bicyclic guanidine reaction product. In certain embodiments, this heating step occurs in a substantially non-hydrocarbon solvent, such as an ethereal solvent or an alcohol solvent, or combinations thereof. Suitable ethereal solvents that may be utilized in the present invention include, without limitation, triethlyene glycol dimethyl ether, diethylene glycol dibutyl ether, tetraethylene glycol dimethyl ether, butyl carbitol formal, or combinations thereof. Suitable alcohols that may be utilized in the present invention include, without limitation, ether functional alcohols, butyl carbitol, ethoxylated bisphenol A polyol, or combinations thereof. In certain embodiments, the ether functional alcohol comprises a glycol ether. Suitable glycol ethers that may be used in the present invention include, without limitation, diethylene glycol monobutyl ether, dipropylene glycol monobutyl ether, propylene glycol butyl ether, or combinations thereof. It should be understood that lower molecular weight, lower boiling ethers, and/or alcohols can be used by running the reaction under pressure, such as up to 2500 psig.

In certain embodiments, the cyclic urea is formed by reacting an (aminoalkyl) amine with a carbonate.

As used herein, the term "(aminoalkyl) amine" refers generally to a compound having the formula $H_2N(CR^3R^4)_nNH(CR^5R^6)_mNH_2$ wherein n and m are independently integers having a value in the range from 2 to 6 and wherein $R^3$, $R^4$, $R^5$, and $R^6$ are independently hydrogen or substituted or unsubstitued alkyl or aryl groups. In addition, the composition of each individual —$CR^3R^4$— and —$CR^5R^6$— unit may also differ from one another. For example, in certain embodiments the $R^3$ group may comprise —$CH_2$— while the R5 group may comprise —$CH_2CH_2CH_2$—. Particularly, suitable (aminoalkyl) amines are those where $R^3$, $R^4$, $R^5$, and $R^6$ are independently hydrogen or a $C_1$-$C_3$ alkyl group. Suitable (aminoalkyl) amines within the formula described in this paragraph and which may be used in the present invention include, without limitation, bis(2-aminoethyl)amine, bis(3-aminopropyl)amine, or combinations thereof.

Suitable carbonates that may be used in the present invention include, without limitation, alkyl and alkylene carbonates such as propylene carbonate, dimethyl carbonate, diethyl carbonate, ethylene carbonate, or combinations thereof.

It should be noted that, in certain embodiments, the reaction mixture that is used to form the cyclic urea can include a non-hydrocarbon solvent, such as those described in the preceding paragraph, or it can include a hydrocarbon solvent such as xylene. Alternatively, in certain embodiments, the reaction mixture that is used to form the cyclic urea is substantially solvent free. As used herein, "substantially solvent free" means that trace or incidental amounts of organic solvent, such as ≦5 weight % or ≦3 weight % or ≦1 weight % based on all of the ingredients used in the reaction mixture, can be present.

In certain embodiments, a catalyst, such as an acid or base catalyst, can be added to the reaction mixture of the (aminoalkyl) amine and the carbonate. Any catalyst known in the art may be used. For example, suitable catalysts include, without limitation, mineral acids, organic acids, Lewis acids, dimethylaminopyridine, imidazole, and TBD.

In certain embodiments, the process begins by charging a reaction vessel with the (aminoalkyl) amine and a solvent. It should be noted that the solvent can either be a hydrocarbon solvent, such as xylene, or a non-hydrocarbon solvent, such as dipropylene glycol monobutyl ether. It should also be noted that in certain embodiments, no solvent is added with the (aminoalkyl) amine.

The total amount of carbonate that may be added to the reaction vessel will depend upon the total amount of (aminoalkyl) amine used in the reaction and can, therefore, be any value, and the rate at which the carbonate is added will be dependent upon the total amount of carbonate that will be added to the reaction vessel. For example, in certain embodiments, the carbonate is added dropwise to this reaction vessel at a rate ranging from 3 grams (g)/minute to 5 g/minute for a total of weight ranging from 120 g to 130 g, such as 124 g.

The reaction vessel is then heated to a temperature and a time period that is sufficient to form the cyclic urea reaction product. In certain embodiments, the reaction vessel is heated to a temperature ranging from $\geq 80°$ C., such as from 80° C. to 100° C., for a time period ranging from 1 hour to 2 hours. After this initial heating step, a non-hydrocarbon solvent, such as those described above, is added to the reaction vessel. The reaction vessel is then heated to $\geq 130°$ C. for a time period ranging from 1 hour to 2 hours thereby forming the cyclic urea reaction product.

In certain embodiments, after the formation of the cyclic urea reaction product, the reaction vessel is heated to a temperature and for a time period sufficient to form the bicyclic guanidine reaction product. In certain embodiments, after the formation of the cyclic urea, the reaction vessel is heated to a temperature >200° C., such as from 218° C., then heated to reflux for a time period ranging from 30 hours to 50 hours, such as 40 hours, thereby forming the bicyclic guanidine reaction product. If a hydrocarbon solvent was used in the steps to form the cyclic urea, it should be noted that the hydrocarbon solvent would be distilled from the reaction vessel prior to the step described in this paragraph. Accordingly, one skilled in the art would recognize that the reaction discussed in this paragraph occurs in the substantially non-hydrocarbon solvent.

After the bicyclic guanidine is formed, it can be isolated by removing the non-hydrocarbon solvent from the reaction vessel. The isolated bicyclic guanidine, which would be in solid form, can then be added to any composition wherein bicyclic guanidine can be used therein. It should also be noted that bicyclic guanidine can also be isolated via precipitation and/or crystallization. Accordingly, in certain embodiments, a solvent, such as heptanes, hexanes, or combinations thereof, is added in which the bicyclic guanidine is insoluble thereby precipitating the bicyclic guanidine.

Alternatively, unisolated bicyclic guanidine may also be admixed with any composition, such as a coating composition, wherein bicyclic guanidine can be used therein. Accordingly, in certain embodiments, the unisolated bicyclic guanidine is cooled to room temperature and a diluent, such as a high-boiling point diluent, is added to the reaction vessel prior to removing the non-hydrocarbon solvent from the reaction vessel. Suitable diluents that may be used in this step include, without limitation, ethoxylated bisphonol A, butyl carbitol formal, or combinations thereof. After removing the non-hydrocarbon solvent from the reaction vessel, the mixture of bicycilc guanidine and diluent may then be admixed with a coating composition, such as an electrodepositable coating composition that is known in the art. For example, in certain embodiments, the bicyclic guanidine formed from the process described herein can be added to the electrodepositable coating composition that is described in U.S. patent application Ser. No. 11/835,600, which is incorporated in its entirety herein by reference.

The process disclosed herein typically produces 1 mole of water for every 1 mole of bicyclic guanidine. Accordingly, in certain embodiments, the water may be removed from the bicyclic guanidine reaction product using techniques known in the art.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

EXAMPLES

Example 1

A 100 mL flask equipped with a reflux condenser and distillation apparatus was purged with nitrogen and was charged with 3,3'-diaminodipropylamine (10 g, 80 mmol), dimethyl carbonate (6.9 g, 80 mmol) and a catalytic amount of 1,5,7-triazabicyclo[4.4.0]dec-5-ene (0.53 g, 3.8 mmol). The mixture was warmed to 130° C. and methanol was distilled out. The reaction was cooled when no more distillate was observed. The resulting light orange oil was identified as N-(3-aminopropyl)-N,N'-trimethyleneurea by $^{13}$C NMR.

Example 2

A 100 mL flask equipped with a steam condenser operating at approximately 100° C. was purged with nitrogen and was charged with N-(3-aminopropyl)-N,N'-trimethyleneurea (5.6 g, 40 mmol) and triethylene glycol dimethyl ether (36 g). This mixture was warmed to 230° C. and held for 56 h. The conversion to 1,5,7-triazabicyclo[4.4.0]dec-5-ene from the starting urea by quantitative $^{13}$C NMR was 94%.

Example 3

A 500 mL flask was fitted with a steam column, distillation head, water-cooled condenser, and collection flask. The reaction vessel was purged with nitrogen and was charged with diethylene glycol dibutyl ether (100.0 g), followed by 3,3'-diaminodipropylamine (40.0 g, 0.310 mol) and 4-(N,N-dimethylamino)pyridine (4.00 g, 0.033 mol). To the stirred solution, propylene carbonate (32.0 g, 0.313 mol) was added and the reaction was allowed to exotherm. After the exotherm, the reaction was heated to 218° C. and held for 4 h, then the temperature was increased to 230° C. and held for 48 h. The yield as determined by HPLC was 55.7%.

Example 4

A 500 mL flask was fitted with a steam column, a xylene filled Dean-Stark trap, and a water-cooled condenser, and collection flask. The reaction vessel was purged with nitrogen and was charged with diethylene glycol dibutyl ether (100.0 g), followed by 3,3'-diaminodipropylamine (20.0 g, 0.153 mol). To the stirred solution, propylene carbonate (16.00 g, 0.157 mol) was added and the reaction was allowed to exotherm. After the exotherm, the reaction was heated to 218° C.

for 4 hours (h), and then the temperature was increased to 230° C. and held for 48 h. The yield as determined by HPLC was 78.2%.

Example 5

A 5 L flask was fitted with a water cooled condenser and the flask was purged with nitrogen. The flask was charged with xylenes (300.0 g) and 3,3'-diaminodipropylamine (180.0 g, 1.37 mol). An 11.6% (w/w) mixture of TBD in butyl carbitol formal was warmed to 100° C. in order to dissolve the TBD, and was added to the reaction vessel hot. Propylene carbonate (142.5 g, 1.40 mol) was added to the stirred solution and the reaction was allowed to exotherm. After the exotherm subsided the reaction was heated to 90° C. for 2 h. The temperature was then raised to 130° C. and was held for 3 h. The reflux condenser was removed and replaced with a steam condenser, a Dean-Stark trap filled with xylenes, and water cooled condenser. The reaction was diluted with of a 1:1 (w/w) mixture of butyl carbitol formal and ethoxylate of bisphenol A (1875.00 g). The reaction was heated to 218° C. for 8 h and was then finally heated to 240° C. for 40 h. The yield as determined by HPLC was 48%.

Example 6

A 1 L flask was fitted with a water cooled condenser and the flask was purged with nitrogen. The flask was charged with 3,3'-diaminodipropylamine (100.0 g, 0.673 mol) and 6.96 g of a 15.4% (w/w) mixture of TBD in butyl carbitol formal that was heated to 100° C. in order to dissolve the TBD. Dimethyl carbonate (70.0 g, 0.777 mol) was added to the stirred solution and the reaction was allowed to exotherm. After the exotherm subsided the reaction was heated to 90° C. for 2 h. The reflux condenser was replaced with a steam condenser, distillation head, and a collection flask, the reaction temperature was then raised to 130° C. The methanol generated by the reaction was distilled off. Tetraethyl ortho silicate (180.0 g, 0.864 mol) was slowly added to reaction over several hours via an addition funnel. After all of the tetraethyl ortho silicate was added, the reaction temperature was raised to 180° C. and was held for 8 h. The temperature was then raised to 230° C. for 30 h and the ethanol evolved from the reaction was distilled off. The yield of the reaction was 35% by HPLC.

Example 7

A 500 mL flask was purged with nitrogen and was charged with 3,3'-diaminodipropylamine (24.0 g, 0.183 mol), xylenes (40.0), and 1.80 g of a 14.4% (w/w) mixture of TBD in butyl carbitol formal that was heated to 100° C. in order to dissolve the TBD. To the stirred solution, propylene carbonate (19.00 g, 0.186 mol) was added and the reaction was allowed to exotherm. After the exotherm, the reaction was heated to 90° C. for 2 h. The reaction was allowed to cool to 70° C. and dipropylene glycol monobutyl ether (250.0 g) was added to the reaction vessel. The reflux condenser was replaced with a steam condenser and xylene filled Dean-Stark trap. The temperature was then held at 218° C. for 6 h. The temperature was then increased to 240° C. and held for 50 h. The yield as determined by HPLC was 90%.

What is claimed is:

1. A method for producing 1,5,7-triazabicyclo[4.4.0]dec-5-ene comprising heating a cyclic urea to a temperature >200° C., wherein the cyclic urea is the reaction product of bis(3-aminopropyl) amine and a carbonate, wherein the carbonate comprises propylene carbonate, dimethyl carbonate, diethyl carbonate, ethylene carbonate, or combinations thereof.

2. The method according to claim 1, wherein the temperature ranges from 218° C. to 250° C.

3. The method according to claim 1, wherein the temperature is ≦250° C.

4. The method according to claim 1, wherein the method further comprises adding a catalyst to the reaction mixture of the bis(3-aminopropyl) amine and the carbonate.

5. The method according to claim 4, wherein the catalyst is an acid catalyst.

6. The method according to claim 5, wherein the acid catalyst comprises mineral acids, organic acids, Lewis acids, or combinations thereof.

7. The method according to claim 4, wherein the catalyst is a base catalyst.

8. The method according to claim 7, wherein the base catalyst comprises dimethylaminopyridine, imidazole, TBD, or combinations thereof.

9. The method according to claim 1, wherein the reaction occurs in an ethereal solvent.

10. The method according to claim 9, wherein the ethereal solvent comprises triethlyene glycol dimethyl ether, diethylene glycol dibutyl ether, butyl carbitol formal, tetraethylene glycol dimethyl ether, diphenyl ether, or combinations thereof.

11. The method according to claim 9, wherein the reaction occurs in an alcohol.

12. The method according to claim 11, wherein the alcohol comprises an ether functional alcohol.

13. The method according to claim 12, wherein the ether functional alcohol comprise a glycol ether.

14. The method according to claim 13, wherein the glycol ether comprises diethylene glycol monobutyl either, dipropylene glycol monobutyl ether, propylene glycol monobutyl ether, tetraethylene glycol monobutyl ether, or combinations thereof.

15. A method for producing 1,5,7-triazabicyclo[4.4.0]dec-5-ene comprising:
  reacting bis(3-aminopropyl) amine with a carbonate to form a cyclic urea, wherein the carbonate comprises propylene carbonate, dimethyl carbonate, diethyl carbonate, ethylene carbonate, or combinations thereof; and
  heating the cyclic urea to a temperature >200° C. in the presence of an ethereal solvent or an alcohol solvent to form 1,5,7-triazabicyclo[4.4.0]dec-5-ene.

16. The method according to claim 15, wherein the method further comprises adding a catalyst to the reaction mixture of the bis(3-aminopropyl) amine and the carbonate.

17. The method according to claim 15, further comprising adding a diluent to the 1,5,7-triazabicyclo[4.4.0]dec-5-ene; wherein the diluent comprises ethoxylated bisphenol A, butyl carbitol formal, or combinations thereof.

18. The method according to claim 15, wherein the temperature ranges from 218° C. to 250° C.

19. The method according to claim 15, wherein the temperature is ≦250° C.

* * * * *